United States Patent
Boyce et al.

(10) Patent No.: US 7,448,264 B2
(45) Date of Patent: Nov. 11, 2008

(54) NON-DESTRUCTIVE METHOD FOR EVALUATING THE STRENGTH OF CANCELLOUS BONE

(75) Inventors: Todd M. Boyce, Aberdeen, NJ (US); David R. Kaes, Toms River, NJ (US); Lawrence A. Shimp, Morganville, NJ (US); John M. Winterbottom, Jackson, NJ (US)

(73) Assignee: Osteotech, Inc., Eatontown, NJ (US)

( * ) Notice: Subject to any disclaimer, the term of this patent is extended or adjusted under 35 U.S.C. 154(b) by 829 days.

(21) Appl. No.: 10/884,097

(22) Filed: Jul. 2, 2004

(65) Prior Publication Data
US 2005/0081619 A1    Apr. 21, 2005

Related U.S. Application Data

(63) Continuation of application No. 10/045,276, filed on Oct. 25, 2001, now abandoned.

(60) Provisional application No. 60/243,170, filed on Oct. 25, 2000.

(51) Int. Cl.
*G01M 19/00* (2006.01)

(52) U.S. Cl. .......................................... 73/172
(58) Field of Classification Search .................... 73/172
See application file for complete search history.

(56) References Cited

U.S. PATENT DOCUMENTS

| 6,442,287 | B1 | 8/2002 | Jiang et al. |
| 6,761,739 | B2 * | 7/2004 | Shepard .................. 623/17.16 |
| 7,124,067 | B2 * | 10/2006 | Ascenzi ........................ 703/11 |

\* cited by examiner

*Primary Examiner*—Edward Lefkowitz
*Assistant Examiner*—Octavia Davis
(74) *Attorney, Agent, or Firm*—Kenneth E. Levitt, Esq.; Dorsey & Whitney LLP (57) ABSTRACT

A non-destructive method for evaluating the strength of cancellous bone includes the steps of performing at least two of the following tests on each cancellous bone of a population of cancellous bones: a manual compression test, an apparent density test, and an appearance test; determining a compressive strength for each cancellous bone based on the two tests performed; comparing the determined compressive strength of each cancellous bone against a predetermined compressive strength requirement; and, eliminating a subset of cancellous bone from the population of cancellous bone, which subset of cancellous bone fails to meet the predetermined compressive strength requirement.

18 Claims, 8 Drawing Sheets

Load at Yield Scatter Plots for the 11 x 14 x 5 mm Group

Fig. 14
Load at Yield Scatter Plots for the
11 x 14 x 13 mm Group

Fig. 15

Load at Yield Scatter Plots With Confidence and Prediction Intervals for 11 x 14 x 5 mm Group

90% Confidence and Prediction Intervals

98% Confidence and Prediction Intervals

Fig. 16

Load at Yield Scatter Plots With Confidence and Prediction Intervals for 11 x 14 x 13 mm Group

NON-DESTRUCTIVE METHOD FOR EVALUATING THE STRENGTH OF CANCELLOUS BONE

CROSS-REFERENCE TO RELATED APPLICATION

The present application is a continuation of U.S. patent application Ser. No. 10/045,276, filed Oct. 25, 2001 now abandoned and claiming the benefit of U.S. provisional application Ser. No. 60/243,170, filed Oct. 25, 2000. The entire contents of application Ser. Nos. 10/045,276 and 60/243,170 are incorporated by reference herein.

BACKGROUND OF THE INVENTION

This application is directed to a method for quickly and easily evaluating the strength of cancellous bone. More specifically, this application is directed to a non-destructive method for quickly and easily evaluating the strength of dense cancellous bone to determine the suitability of the cancellous bone for use in a particular surgical application. The application is also directed to a cancellous bone implant and method for its manufacture.

The use of bone allografts in surgical procedures for repairing bone fractures, torn ligaments, spinal disorders, etc., is well known in the art. Examples of such allografts, designed specifically for use in spinal fusion procedures, are disclosed in U.S. Pat. Nos. 6,527,773 and 6,638,310, the entire contents of which are incorporated by reference herein.

The strength and quality of bone, particularly cancellous bone, varies greatly from donor to donor, and also from location to location within a single donor. For example, studies have shown that the apparent density of cancellous bone decreases significantly with age and that the apparent density of bone varies between genders. As the apparent density of bone decreases, the compressive strength, and thus the load bearing capacity, of the bone also decreases.

In a laboratory environment, the compressive strength of allograft bone can be determined using the appropriate machinery to subject the bone to a compressive force until failure occurs, e.g., as described in U.S. Pat. No. 6,442,287. Although the compressive strength of a particular specimen of cancellous bone can be determined using this method, such a method is impracticable. Firstly, using this method, the particular specimen tested is destroyed. Secondly, the compressive strength of the specimen tested is not determinative of the compressive strength of cancellous bone from a different, or even the same, donor.

As discussed above, cancellous bone allografts are used in a variety of surgical procedures including spinal fusion procedures, e.g., fusion procedures in the cervical region of the spine. In a spinal fusion procedure, at least a portion of the disc between adjacent vertebrae is removed and an allograft is positioned between adjacent vertebral endplates to retain and support the vertebrae at a fixed location with respect to each other. It is imperative to the success of such a procedure that the allograft be capable of withstanding the compressive forces generated by the vertebrae.

Accordingly, an improved method for determining the strength of allografts formed of cancellous bone is needed which does not destroy the bone and which can be easily and quickly performed by a technician.

BRIEF SUMMARY OF THE INVENTION

A non-destructive method for evaluating the strength of cancellous bone, includes the steps of performing at least two of the following test on each cancellous bone of a population of cancellous bones, namely, a manual compression test, an apparent density test, and an appearance test; determining a compressive strength for each cancellous bone based on the two tests performed; comparing the determined compressive strength of each cancellous bone against a predetermined compressive strength requirement; and eliminating a subset of cancellous bone from the population of cancellous bone, which subset of cancellous bone fails to meet the predetermined compressive strength requirement.

The manual compression test includes the steps of manually compressing each cancellous bone to make a subjective determined of the compressive strength of each cancellous bone and removing a cancellous bone from the population of cancellous bones when the manually compressed cancellous bone appreciably deforms. The appearance test includes the steps of assessing a quality of each cancellous bone based on their individual appearance and assigning each cancellous bone with a grade which designates a subjective quality assessment of each cancellous bone. The apparent density test includes the steps of cleaning each cancellous bone, freeze drying each cancellous bone, measuring the dimensions of each cancellous bone to determine volume thereof, weighing each cancellous bone, determining an apparent density for each cancellous bone, and determining the compressive strength of each cancellous bone based on the apparent density.

BRIEF DESCRIPTION OF THE DRAWINGS

FIG. 1 illustrates the cancellous bone orientation in the proximal femur; and, FIGS. 2-12 illustrates the location and direction of first facing cuts for a variety of donor bones; and, FIGS. 13-16 are graphs of test data obtained from the compressive testing of each specimens within two groups of cervical spacers.

DETAILED DESCRIPTION OF THE INVENTION

Preferred embodiments of the presently disclosed non-destructive method for evaluating cancellous bone strength of allograft tissue will now be described.

The presently disclosed non-destructive method for evaluating the strength of cancellous allograft bone tissue includes at least two of three separate tests, the tests being performed by a technician during preparation of the allograft. These tests include the appearance test, the manual compression test and the apparent density test. Each test is used to determine or identify a subset of cancellous bone allografts which have better strength than those of the overall population of cancellous allografts.

Initially, a cancellous bone allograft is cut from cancellous donor bone into a desired implant configuration which may be that of a cylindrical dowel, wedge, rectangular spacer, etc. Prior to cutting, the donor bone may be cleaned using an external spray to remove soft tissue from its external surface. The bone may be cut such that the first facing cut or cuts (which will become either the top or bottom loading surface of the implant) is/are perpendicular to the trabecular orientation of the bone. Typically, these facing cuts will be perpendicular to the long axis of the bone. In this way, the resulting implant will be loaded in a similar orientation to the loading orientation of the bone donor's lifetime.

When cancellous bone is formed (in the donor bone), it is aligned along the direction of loading. This puts the cancellous bone in the best location and orientation to support loads in the likely directions. Load is transferred from the articular surface (covered with cartilage, where it forms a joint with another bone) through this cancellous bone to the cortical shell where it is carried to the other end. Early researchers, including John Koch (1917) noticed distinctive patterns in the proximal femur and found through engineering calculations that stresses within the femur-head corresponds to the architecture of the cancellous bone. The body naturally places bone where it will be loaded and removes bone from places where it will not be loaded. This naturally-occurring orientation of bone in the direction of loading is the basis for selecting the location and direction of the cuts to be made to a particular allograft bone to provide the desired implant.

The implant of this invention is cut from the cancellous region of donor bone so that the resulting structure will possess two opposed load-bearing (load-supporting) surfaces, such surfaces being generally perpendicular to the natural orientation of the cancellous bone in the direction of loading in compression.

Figure 1:
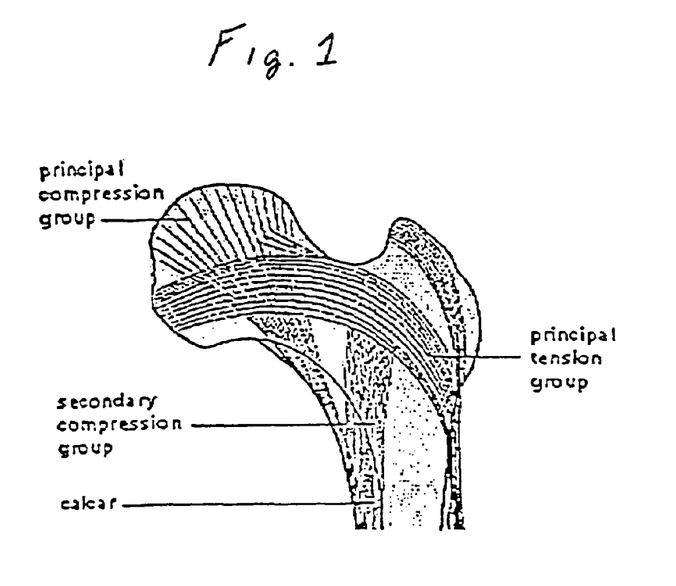
Figure 2:
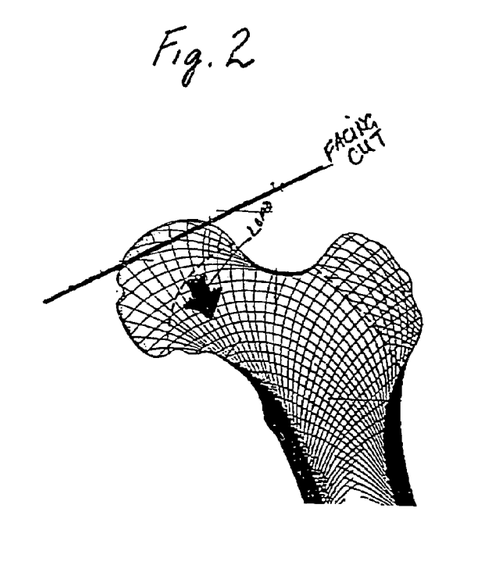
Figure 3:
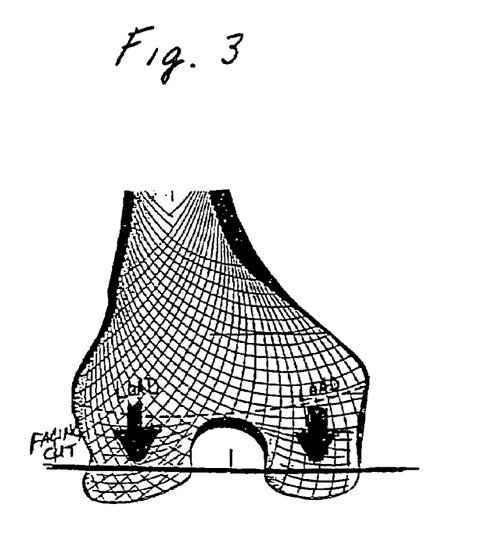
Figure 4:
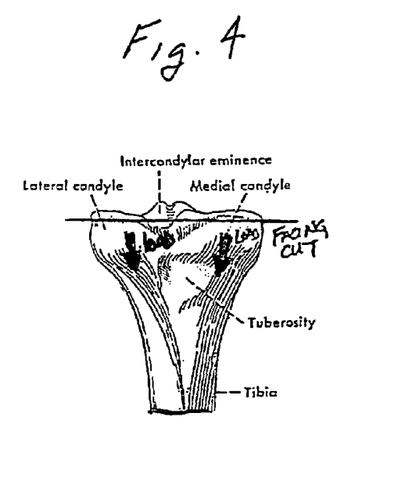
Figure 5:
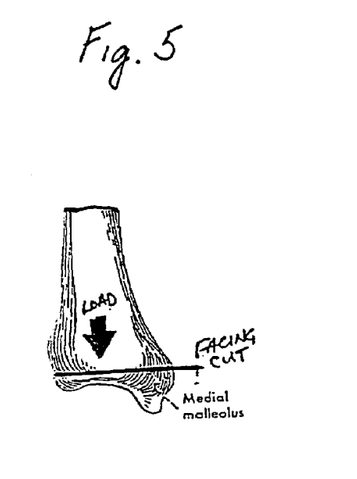
Figure 6:
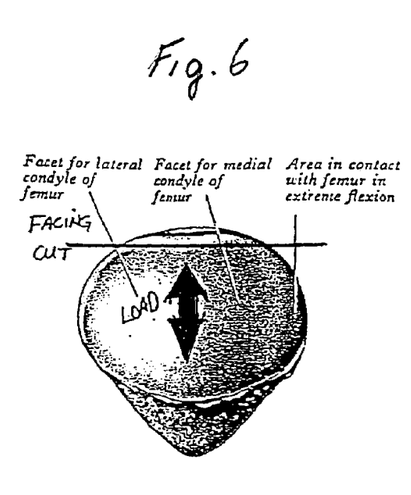
Figure 7:
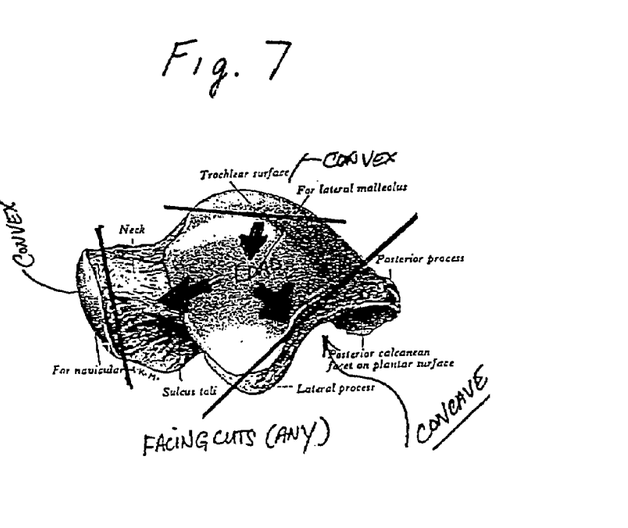
Figure 8:
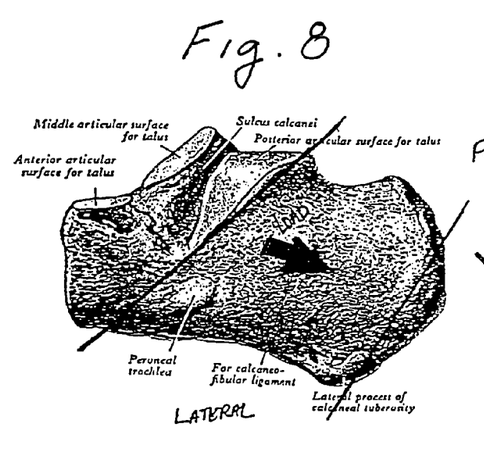
Figure 9:
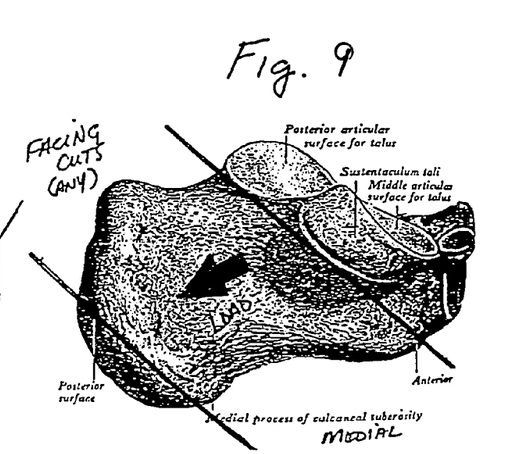

FIG. 1 is a sectional view of a proximal femur characterized by a region of cancellous bone, the orientation of which is represented by the curvilinear lines. In cutting the desired implant, e.g., cervical spacer, the essential requirement of the cutting procedure is to make the first, facing cut (which will produce the top or bottom load-receiving surface of the cervical spacer) generally perpendicular to the trabecular orientation in the bone. This is usually perpendicular to the long axis of the bone. Once the first facing out has been made, the finishing cut can then be made in appropriate relationship to it to provide the second load-bearing surface of the cervical spacer.

Figure 10:
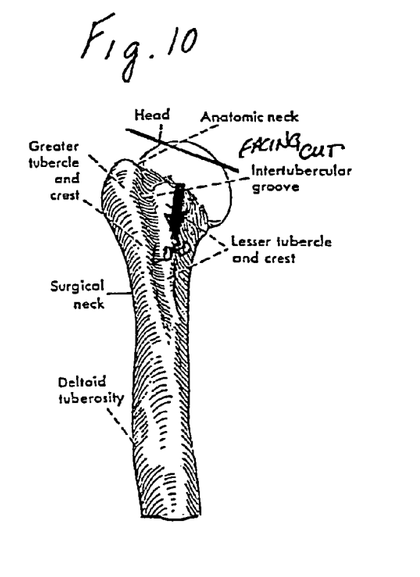
Figure 11:
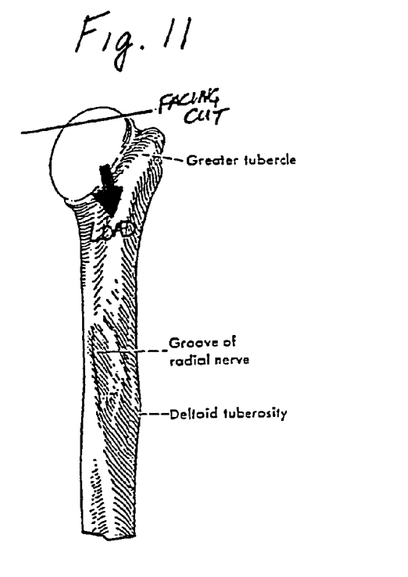
Figure 12:
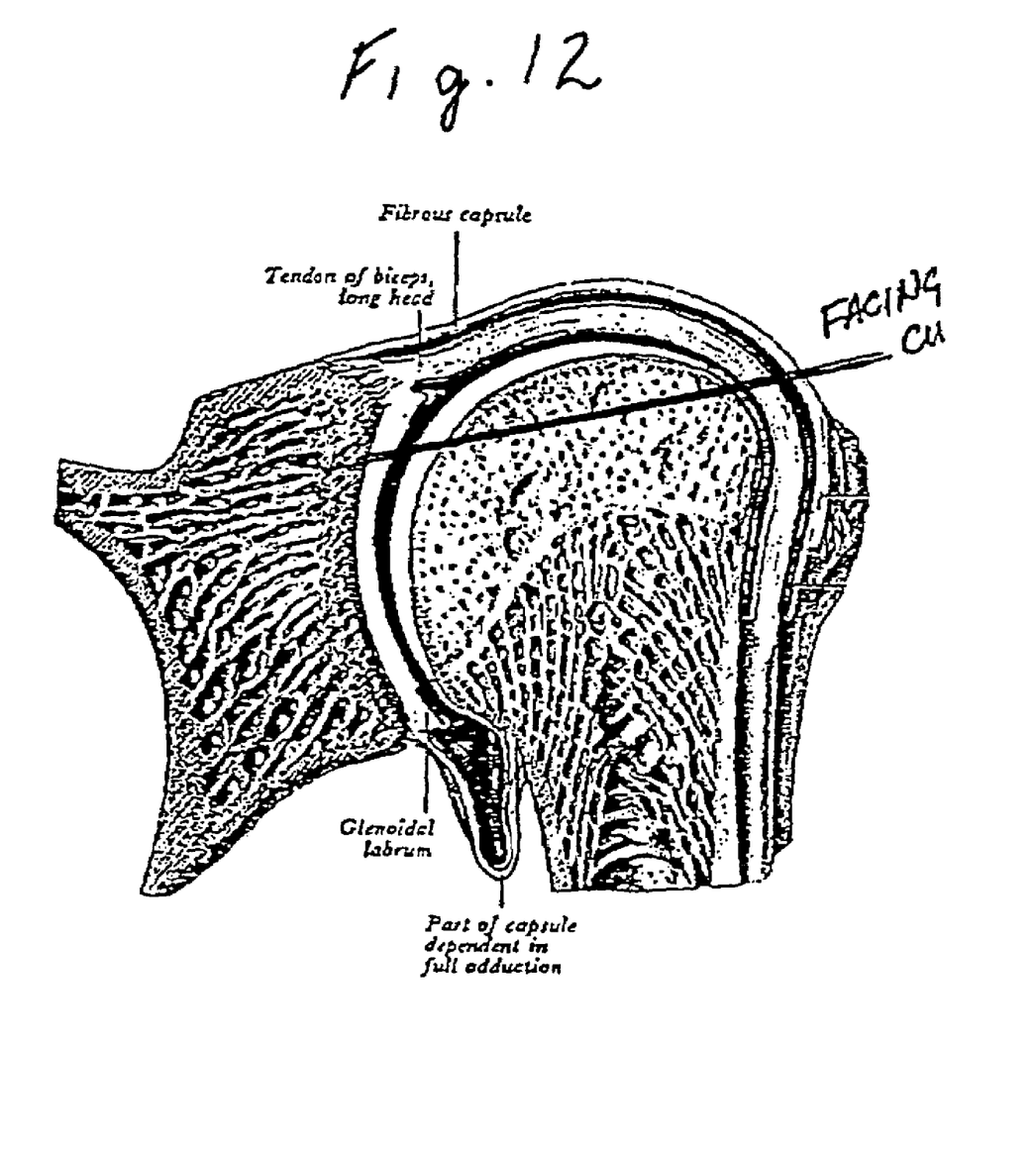

FIGS. 2-12 herein illustrate the loading distributions (shown by the arrows) and the location and orientation of first facing cuts that may be made to a variety of different donor bones, specifically, the proximal femur (FIG. 2), the distal femur (FIG. 3), the proximal tibia (FIG. 4), the distal tibia (FIG. 5), the patella (FIG. 6), the talus (FIG. 7), the lateral and medial processes of the calcaneal tuberosity (FIGS. 8 and 9, respectively) and the humerus (FIGS. 10-12).

After the allograft has been cut into a desired configuration, a technician will perform at least two of the above-identified tests and make the attendant evaluations. The manual compression test may be performed prior to or after cleaning of the bone but must be performed prior to freeze drying the allograft. In conducting the manual compression test, the cancellous bone allograft is compressed between the technician's fingers to make a subjective determination of the hardness and the compressive strength of the cancellous bone allograft. The manual compression test provides a first level of allograft screening. If the allograft compresses appreciably or deforms greatly between the fingers of a technician, the allograft is discarded. Discarded allograft bone can be used to form other osteoinductive materials or compounds. Using the manual compression test, trained technicians can consistently eliminate grafts which fall below a minimum required compressive strength. The minimum required compressive strength of the graft will vary according to the intended use of the graft, e.g., the minimum required compressive strength of a graft for use in the cervical spine is approximately 500 newtons.

After the manual compression test has been conducted and the cancellous bone allograft has been cleaned by removing the blood and marrow from the bone, the technician performs the visual appearance test. The appearance test can be conducted prior to or after freeze drying the bone. In conducting the appearance test, a technician assesses the quality of the allograft based on its appearance to determine if the allograft meets the standard of "dense cancellous bone". The technician will assign the load bearing allograft a rating using a Grade 1 to Grade 5 scale (1 being the most suitable for allograft use and 5 being the least suitable) to designate the technician's subjective quality assessment of the cancellous bone allograft.

Table 1 below set forth the typical appearance characteristics of a cervical spacerallograft for each of Grades 1 to Grade 5:

TABLE 1

CERVICAL SPACER ALLOGRAFT
VISUAL APPEARANCE CHARACTERISTICS

Grade 1

All flat surfaces have a uniform appearance and show very little porosity.
Where visible, pores are very small and do not penetrate deeply into the implant.
All implant edges are sharp and well defined.
Very little or no discernable visual variation in density throughout the implant.

Grade 2

Some flat surfaces of the implant appear slightly more porous than in Grade 1.
Pores are small and do not penetrate deeply into the implant.
Most implant edges are sharp and well defined, with some showing slight serration when passing through small pores.
Overall porosity is only slightly more than in Grade 1 and distributed fairly evenly throughout the surface of the implant.

Grade 3

Pores on flat surfaces are slightly larger, vary more in size and shape, and are distributed more unevenly than in Grade 2.
Edges tend to be less well defined. Some edges have a wavy appearance due to passing through larger size pores.
Overall implant porosity is not uniform in appearance. Some regions of the implant are noticeably more porous in appearance than others.
In some regions of the implant, pores are larger and reach deeper into the implant than in Grade 2.

Grade 4

Pores on flat surfaces are larger and deeper than those described in Grade 3.
Large pores are present over the majority of the implant surface.
Edges and corners are not well defined and tend to be rounded in appearance.
Most edges are interrupted where crossing large pores.
Pores on flat surfaces appear to be more prevalent than bone. Edges of the implant appear translucent.
Majority of the implant's surface has a web-like appearance.
Implant looks fragile.

Grade 5

Pores are so large and more prevalent than bone that the surfaces and body of the implant has a net-like appearance.
Body of implant appears to be almost transparent.
Edges are not well defined and have small thread-like protrusions.
Chamfer edges are very hard to discern.
Implant looks extremely fragile.

Finally, an apparent density test of the cancellous bone allograft is conducted to estimate the strength of the allograft. More specifically, each allograft is weighed and its dimensions are measured to determine the volume of the allograft (including the volume of the pore spaces). Knowing the weight and volume, the apparent density of the allograft can be easily determined. The apparent density test of each allograft should be conducted after the allograft has been cleaned, the cleaning solution has been removed from the allograft and the allograft has been freeze dried. Alternately, the apparent density test can be conducted prior to freeze drying the allograft. It is noted that if cancellous bone allografts are cut to specific dimensions, each allograft need not be measured independently but rather the volume of the allograft can be determined based on the pre-selected dimensions of the allograft. If the apparent density test is conducted prior to freeze drying, some process should be used to reduce the water content in the allograft bone to a predetermined level such that the volume of water remaining in the cancellous bone can be factored into the apparent density measurement. Using known data obtained through prior testing of a statistically significant number of cancellous bone samples, a graph can be plotted comparing compressive strength of cancellous bone v. apparent density of the cancellous bone. Using this graph, the compressive strength of a cancellous bone graft can be estimated after the apparent density of the graft has been determined. If the allograft has passed the manual compression test, the appearance test and has the required apparent density, the allograft is acceptable for allograft use.

EXAMPLE

This example illustrates the compressive testing of a number of machine-cut, chamfered, rectangular, freeze-dried cervical spacer implant specimens (from 5 donors) to demonstrate the relationship between their apparent density and compressive strength. Two groups of specimens were tested:

11 mm×14 mm×5 mm (L×W×H), V.I. treated, freeze-dried, machine-cut dense cancellous 11 mm×14 mm×13 mm (L×W×H), V.I. treated freeze-dried, machine-cut dense cancellous The test specimens were placed in physiological saline at ambient temperature for 30 minutes prior to testing. Compressive tests were performed no more than 5 minutes from the time that each specimen was removed from the saline fluid. Specimens were preloaded (under load control) to 10 N of compressive load. Machine axial displacement was then zeroed at this preload.

The testing equipment used was the MTS model 858 Bionix materials testing system. The system load cell (±100 kN) operated in the ±10 kN load range, and the system actuator-mounted LVDT was used to collect load and displacement information. Testworks version 4 software was used for load displacement data acquisition and storage and machine control.

Specimens were loaded using a ramp waveform at a constant rate of 25 mm/minute in displacement control mode. A total displacement of 3 mm was applied to the 11×14×13 mm test specimens and a total displacement of 2 mm was applied to specimens in the 11×14×5 mm group.

The terms "density" and "calculated density" in this example refer to apparent density calculated from the measured weights and dimensions presented in Table 2 below. The term "nominal density" refers to apparent density calculated using specimen weight and the nominal dimensions for that implant size (e.g. volume calculated using 11×14×5 mm with 2.11 mm chamfer). The term "absolute error" refers the absolute value of the difference between a regression equation prediction for a specimen load at yield value, and the actual load at yield value obtained from the compressive testing of that specimens.

TABLE 2

PROPERTIES OF TEST SPECIMENS

| Specimen Number | Dry wt, g | Freeze-Dry Dimensions (mm) | | | | Wet Wt., g |
|---|---|---|---|---|---|---|
| | | Width | Length | Height | Chamfer Length | |
| A. 11 × 14 × 5 mm Test Specimens | | | | | | |
| 1A | 0.5719 | 13.46 | 11.26 | 5.41 | 1.95 | 0.8157 |
| 2A | 0.4804 | 13.48 | 11.21 | 5.4 | 1.99 | 0.6851 |
| 3A | 0.4539 | 13.59 | 11.3 | 5.36 | 2.03 | 0.7131 |
| 4A | 0.4973 | 13.51 | 11.36 | 5.37 | 2.08 | 0.703 |
| 5A | 0.4892 | 13.42 | 11.19 | 5.29 | 1.97 | 0.7186 |
| 6A | 0.5131 | 13.42 | 11.24 | 5.31 | 1.95 | 0.7208 |
| 7A | 0.5113 | 13.52 | 11.48 | 5.34 | 2.02 | 0.7985 |
| 8A | 0.4175 | 13.56 | 11.09 | 5.36 | 1.93 | 0.6233 |
| 9A | 0.4185 | 13.56 | 11.36 | 5.33 | 2.02 | 0.5909 |
| 10A | 0.4044 | 13.48 | 11.37 | 5.35 | 2.05 | 0.5777 |
| 11A | 0.4517 | 13.51 | 11.01 | 5.33 | 1.93 | 0.6135 |
| 12A | 0.2965 | 13.49 | 11.11 | 5.29 | 1.98 | 0.4125 |
| 13A | 0.4521 | 13.69 | 11.43 | 5.36 | 1.97 | 0.7367 |
| 14A | 0.6901 | 13.63 | 11.39 | 5.39 | 2.02 | 0.9639 |
| 15A | 0.644 | 13.53 | 11.51 | 5.39 | 1.99 | 0.9553 |
| 16A | 0.5795 | 13.77 | 11.28 | 5.39 | 2.05 | 0.8495 |
| 17A | 0.4828 | 13.64 | 11.47 | 5.36 | 1.95 | 0.751 |
| 18A | 0.5875 | 13.5 | 11.49 | 5.39 | 2.04 | 0.8423 |
| 19A | 0.6096 | 13.62 | 11.52 | 5.3 | 2 | 0.874 |
| 20A | 0.6867 | 13.57 | 11.43 | 5.34 | 2.07 | 0.9322 |
| 21A | 0.6555 | 13.55 | 11.5 | 5.32 | 1.95 | 0.9056 |
| 22A | 0.6137 | 13.67 | 11.48 | 5.38 | 2.03 | 0.8267 |
| 23A | 0.6578 | 13.6 | 11.57 | 5.31 | 1.97 | 0.9231 |
| 24A | 0.462 | 13.52 | 11.46 | 5.36 | 1.98 | 0.6494 |
| 25A | 0.3892 | 13.59 | 11.4 | 5.34 | 1.93 | 0.6348 |
| 26A | 0.4305 | 13.57 | 11.37 | 5.25 | 1.95 | 0.7543 |
| 27A | 0.5592 | 13.65 | 11.53 | 5.31 | 2.07 | 0.8759 |
| 28A | 0.4418 | 13.55 | 11.41 | 5.31 | 2.11 | 0.7321 |
| 29A | 0.3998 | 13.57 | 11.33 | 5.24 | 2.09 | 0.7025 |
| 30A | 0.5039 | 13.57 | 11.43 | 5.32 | 2.07 | 0.7949 |

TABLE 2-continued

PROPERTIES OF TEST SPECIMENS

| Specimen Number | Dry wt, g | Freeze-Dry Dimensions (mm) | | | | Wet Wt., g |
|---|---|---|---|---|---|---|
| | | Width | Length | Height | Chamfer Length | |
| Mean | 0.511713 | 13.55967 | 11.366 | 5.34 | 2.004667 | 0.755897 |
| S.D. | 0.099678 | 0.078717 | 0.140433 | 0.042508 | 0.052898 | 0.128361 |
| B. 11 × 14 × 13 Test Specimens | | | | | | |
| 1B | 1.3996 | 13.52 | 11.43 | 13.55 | 2.07 | 2.1905 |
| 2B | 1.3090 | 13.52 | 11.48 | 13.65 | 2.13 | 2.4164 |
| 3B | 1.2867 | 13.52 | 11.40 | 13.55 | 2.06 | 1.9529 |
| 4B | 1.4566 | 13.57 | 11.35 | 13.52 | 1.93 | 2.202 |
| 5B | 1.2842 | 13.53 | 11.39 | 13.56 | 1.95 | 2.3185 |
| 6B | 1.1076 | 13.53 | 11.22 | 13.54 | 1.86 | 2.066 |
| 7B | 0.8035 | 13.56 | 11.53 | 12.98 | 1.91 | 1.2182 |
| 8B | 0.9357 | 13.62 | 11.35 | 13.53 | 1.96 | 1.4653 |
| 9B | 1.1536 | 13.56 | 11.47 | 13.55 | 2.15 | 1.7205 |
| 10B | 1.0365 | 13.53 | 11.43 | 13.64 | 2.03 | 1.5012 |
| 11B | 0.9381 | 13.63 | 11.32 | 13.55 | 2.05 | 1.4747 |
| 12B | 1.0036 | 13.55 | 11.31 | 13.60 | 1.99 | 1.5586 |
| 13B | 1.145 | 13.65 | 11.38 | 13.57 | 1.96 | 2.1268 |
| 14B | 1.5109 | 13.63 | 11.38 | 13.60 | 1.99 | 2.3367 |
| 15B | 1.6636 | 13.65 | 11.51 | 13.64 | 1.95 | 2.551 |
| 16B | 1.2844 | 13.29 | 11.39 | 13.68 | 2.05 | 2.0297 |
| 17B | 1.4134 | 13.58 | 11.40 | 13.62 | 1.97 | 2.3757 |
| 18B | 1.2171 | 13.58 | 11.48 | 13.66 | 2.04 | 2.1676 |
| 19B | 1.0554 | 13.51 | 11.34 | 13.61 | 2.02 | 1.8207 |
| 20B | 1.556 | 13.59 | 11.52 | 13.57 | 2.01 | 2.2806 |
| 21B | 1.3559 | 13.56 | 11.48 | 13.55 | 2.05 | 1.9399 |
| 22B | 0.9797 | 13.56 | 11.39 | 13.61 | 1.98 | 1.4293 |
| 23B | 1.3526 | 13.58 | 11.49 | 13.62 | 2.05 | 1.883 |
| 24B | 1.4141 | 13.54 | 11.48 | 13.53 | 2.00 | 2.0934 |
| 25B | 1.6105 | 13.60 | 11.32 | 13.65 | 2.06 | 2.4965 |
| 26B | 1.5183 | 13.60 | 11.36 | 13.61 | 2.09 | 2.4276 |
| 27B | 1.4155 | 13.63 | 11.55 | 13.68 | 1.97 | 2.1853 |
| 28B | 1.228 | 13.63 | 11.50 | 13.71 | 2.02 | 1.8588 |
| 29B | 1.0113 | 13.53 | 11.35 | 13.62 | 1.98 | 1.9487 |
| 30B | 1.0706 | 13.55 | 11.27 | 13.63 | 1.91 | 1.9538 |
| Mean | 1.250567 | 13.563433 | 11.409 | 13.57933 | 2.006333 | 1.999663 |
| S.D. | 0.223891 | 0.066661 | 0.082602 | 0.124067 | 0.065257 | 0.352698 |

The test results for all of the specimens are set forth in Table 3 below:

TABLE 3

RESULTS OF COMPRESSIVE TESTING

| Specimen Number | Load At Yield N | Extension At Yield mm | Calculated Density (g/cc) | Nominal Density (g/cc) |
|---|---|---|---|---|
| A. 11 × 14 × 5 mm Specimens | | | | |
| 1A | 2420.8 | 0.3626 | 0.7154 | 0.7648 |
| 2A | 1441.4 | 0.4317 | 0.6046 | 0.6425 |
| 3A | 1082.4 | 0.3378 | 0.5666 | 0.6070 |
| 4A | 1815.8 | 0.3790 | 0.6209 | 0.6651 |
| 5A | 1561.0 | 0.2767 | 0.6321 | 0.6542 |
| 6A | 1960.6 | 0.2052 | 0.6572 | 0.6862 |
| 7A | 1485.1 | 0.4222 | 0.6336 | 0.6838 |
| 8A | 1145.4 | 0.4599 | 0.5311 | 0.5583 |
| 9A | 1116.9 | 0.3635 | 0.5236 | 0.5597 |
| 10A | 1102.5 | 0.4039 | 0.5071 | 0.5408 |
| 11A | 1478.5 | 0.4209 | 0.5844 | 0.6041 |
| 12A | 680.4 | 0.3618 | 0.3840 | 0.3965 |
| 13A | 497.6 | 0.3266 | 0.5527 | 0.6046 |
| 14A | 3501.4 | 0.4228 | 0.8470 | 0.9229 |
| 15A | 3174.1 | 0.2670 | 0.7872 | 0.8613 |
| 16A | 896.0 | 0.4757 | 0.7114 | 0.7750 |
| 17A | 715.5 | 0.3876 | 0.5901 | 0.6457 |
| 18A | 2798.7 | 0.2670 | 0.7221 | 0.7857 |
| 19A | 1005.9 | 0.3608 | 0.7522 | 0.8153 |
| 20A | 3098.1 | 0.3237 | 0.8526 | 0.9184 |
| 21A | 3256.6 | 0.3792 | 0.8105 | 0.8766 |
| 22A | 3470.1 | 0.2545 | 0.7465 | 0.8207 |
| 23A | 3558.2 | 0.2545 | 0.8072 | 0.8797 |
| 24A | 1611.7 | 0.2180 | 0.5708 | 0.6179 |
| 25A | 1347.2 | 0.2216 | 0.4820 | 0.5205 |
| 26A | 1493.6 | 0.3470 | 0.5449 | 0.5757 |
| 27A | 2547.3 | 0.3213 | 0.6879 | 0.7479 |
| 28A | 1124.2 | 0.2204 | 0.5541 | 0.5908 |
| 29A | 805.6 | 0.2224 | 0.5108 | 0.5347 |
| 30A | 1235.7 | 0.2041 | 0.6280 | 0.6739 |
| Mean | 1780.9 | 0.3300 | 0.6373 | 0.6843 |
| Std. Dev. | 953.8 | 0.0817 | 0.1178 | 0.1333 |
| B. 11 × 14 × 13 mm Specimens | | | | |
| 1B | 1876.9 | 0.3510 | 0.6875 | 0.7199 |
| 2B | 2576.3 | 0.4487 | 0.6365 | 0.6733 |
| 3B | 1383.1 | 0.4171 | 0.6336 | 0.6618 |
| 4B | 1964.6 | 0.3750 | 0.7168 | 0.7492 |
| 5B | 2331.2 | 0.4188 | 0.6301 | 0.6606 |
| 6B | 1360.2 | 0.3060 | 0.5514 | 0.5697 |
| 7B | 831.9 | 0.9466 | 0.4054 | 0.4133 |
| 8B | 656.7 | 0.3632 | 0.4588 | 0.4813 |
| 9B | 1578.2 | 0.6423 | 0.5642 | 0.5934 |
| 10B | 1095.2 | 0.4748 | 0.5048 | 0.5331 |
| 11B | 869.9 | 0.4021 | 0.4613 | 0.4825 |
| 12B | 845.0 | 0.4345 | 0.4943 | 0.5162 |

TABLE 3-continued

RESULTS OF COMPRESSIVE TESTING

| Specimen Number | Load At Yield N | Extension At Yield mm | Calculated Density (g/cc) | Nominal Density (g/cc) |
|---|---|---|---|---|
| 13B | 1107.7 | 0.3034 | 0.5570 | 0.5890 |
| 14B | 2173.5 | 0.3793 | 0.7350 | 0.7772 |
| 15B | 2673.0 | 0.5197 | 0.7955 | 0.8557 |
| 16B | 1596.5 | 0.3216 | 0.6380 | 0.6607 |
| 17B | 1905.1 | 0.4318 | 0.6876 | 0.7270 |
| 18B | 901.6 | 0.3465 | 0.5872 | 0.6260 |
| 19B | 1605.9 | 0.3749 | 0.5200 | 0.5429 |
| 20B | 1683.1 | 0.3342 | 0.7518 | 0.8004 |
| 21B | 1693.2 | 0.4482 | 0.6607 | 0.6974 |
| 22B | 1278.3 | 0.3760 | 0.4782 | 0.5039 |
| 23B | 1570.6 | 0.4015 | 0.6541 | 0.6957 |
| 24B | 1422.3 | 0.3125 | 0.6902 | 0.7274 |
| 25B | 1707.8 | 0.4621 | 0.7881 | 0.8284 |
| 26B | 2247.4 | 0.4684 | 0.7431 | 0.7810 |
| 27B | 1434.6 | 0.5720 | 0.6739 | 0.7281 |
| 28B | 1287.7 | 0.4672 | 0.5867 | 0.6316 |
| 29B | 532.1 | 0.2229 | 0.4962 | 0.5202 |
| 30B | 700.2 | 0.2395 | 0.5269 | 0.5507 |
| Mean | 1496.3 | 0.4187 | 0.6105 | 0.6433 |
| Std. Dev. | 565.6 | 0.1338 | 0.1061 | 0.1152 |

Tables 4-8 below each present additional test data for the specimens in each group:

TABLE 4

TWO-SAMPLE T-TEST ASSUMING EQUAL VARIANCES, LOAD AT YIELD

| | 11 × 14 × 5 mm | 11 × 14 × 13 mm |
|---|---|---|
| Mean (N) | 1780.9 | 1496.3 |
| Variance | 909769.5 | 319942.1 |
| Observations | 30 | 30 |
| Pooled Variance | 614855.8 | |
| Hypothesized Mean Difference | 0 | |
| df | 58 | |
| t Stat | 1.4057 | |
| P(T <= t) one-tail | 0.0826 | |
| t Critical one-tail | 1.6716 | |
| P(T <= t) two-tail | 0.1651 | |
| t Critical two-tail | 2.0017 | |

TABLE 5

TWO-SAMPLE T-TEST ASSUMING EQUAL VARIANCES, DISPLACEMENT AT YIELD

| | 11 × 14 × 5 mm | 11 × 14 × 13 mm |
|---|---|---|
| Mean (mm) | 0.3300 | 0.4187 |
| Variance | 0.0067 | 0.0179 |
| Observations | 30 | 30 |
| Pooled Variance | 0.0123 | |
| Hypothesized Mean Difference | 0 | |
| df | 58 | |
| t Stat | −3.10035 | |
| P(T <= t) one-tail | 0.00149 | |
| t Critical one-tail | 1.67155 | |
| P(T <= t) two-tail | 0.00298 | |
| t Critical two-tail | 2.00172 | |

TABLE 6

COMPARISON OF LOAD AT YIELD MEANS FOR HAND-CUT AND MACHINE-CUT SPECIMENS, DIFFERING IN CROSS-SECTIONAL AREA

| | 11 × 14 × 5 (068) | 11 × 11 × 5 mm (063) |
|---|---|---|
| Mean (N) | 1780.9 | 1426.3 |
| Variance | 909769.5 | 293973.4 |
| Observations | 30 | 31 |
| Pooled Variance | 596652.9 | |
| Hypothesized Mean Difference | 0 | |
| df | 59 | |
| t Stat | 1.7929 | |
| P(T <= t) one-tail | 0.0391 | |
| t Critical one-tail | 1.6711 | |
| P(T <= t) two-tail | 0.0781 | |
| t Critical two-tail | 2.0010 | |

TABLE 7

SUMMARY OF ABSOLUTE ERROR CALCULATIONS FOR DIFFERING PREDICTION TYPES

| Prediction Type Reg. Eqn. predicts Population | Average Absolute Error (N) | Sum of Absolute Error (N) |
|---|---|---|
| 13 mm predicts 13 mm | 282 | 8458 |
| All 068 predicts 13 mm | 298 | 8946 |
| 5 mm predicts 13 mm | 345 | 10353 |
| 5 mm predicts 5 mm | 403 | 12075 |
| All 068 predicts 5 mm | 427 | 12810 |
| 13 mm predicts 5 mm | 484 | 14532 |

TABLE 8

TWO-SAMPLE T-TEST ASSUMING EQUAL VARIANCES, CROSS-PREDICTION ABSOLUTE ERROR

| | 5 mm Predicts 13 mm | 13 mm Predicts 5 mm |
|---|---|---|
| Mean (N) | 345.1 | 484.4 |
| Variance | 68414.0 | 160008.7 |
| Observations | 30 | 30 |
| Pooled Variance | 114211.3 | |
| Hypothesized Mean Difference | 0 | |
| df | 58 | |
| t Stat | −1.5968 | |
| P(T <= t) one-tail | 0.0579 | |
| t Critical one-tail | 1.6716 | |
| P(T <= t) two-tail | 0.1158 | |
| t Critical two-tail | 2.0017 | |

As these data show, increasing the cross-sectional area of the 5 mm high implant increases the compressive load at yield (p<0.05, Table 5). Although not statistically significant (p>0.05, Table 3), the larger height implant tends to have a slightly lower average load at yield.

Figure 13:
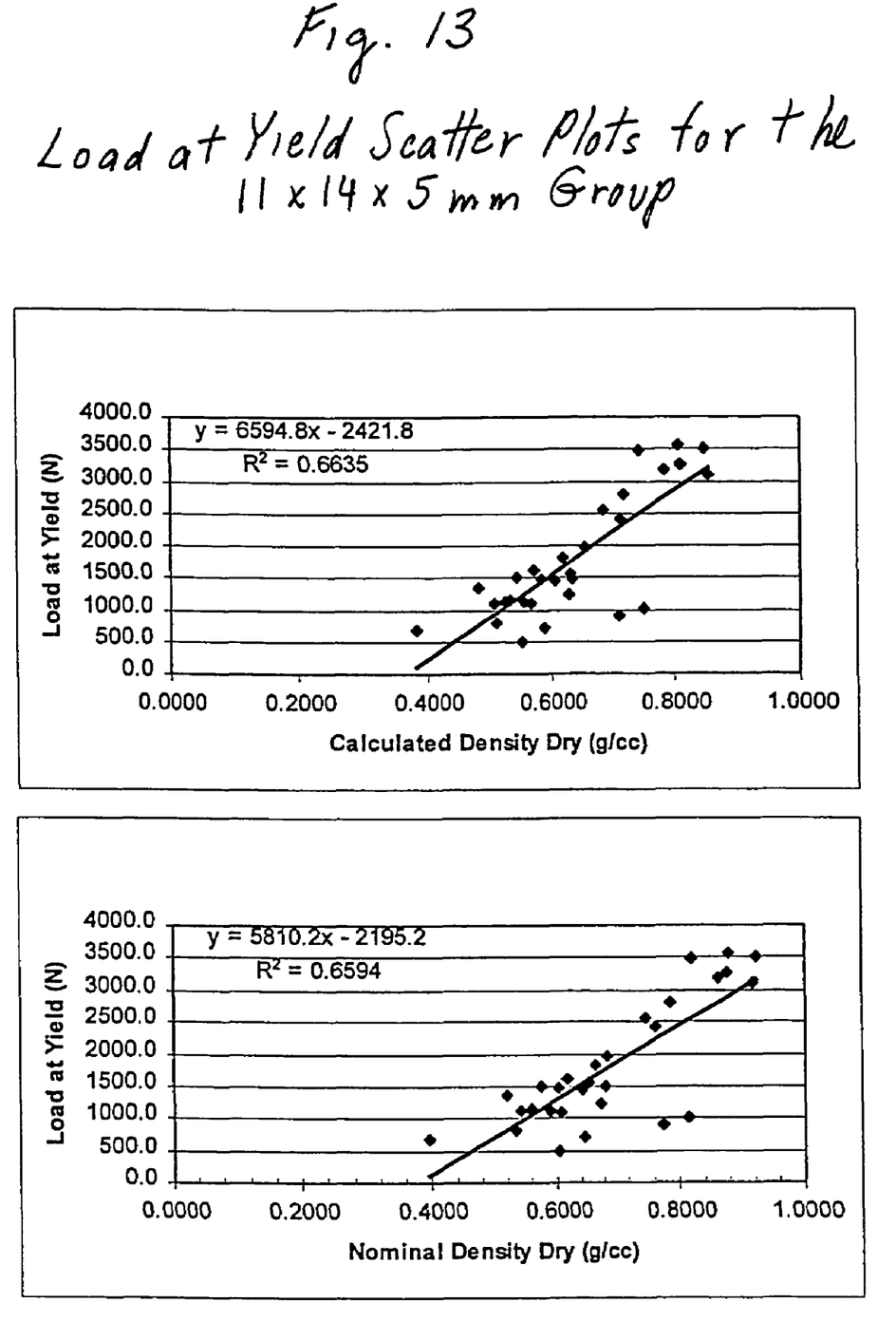
Figure 14:
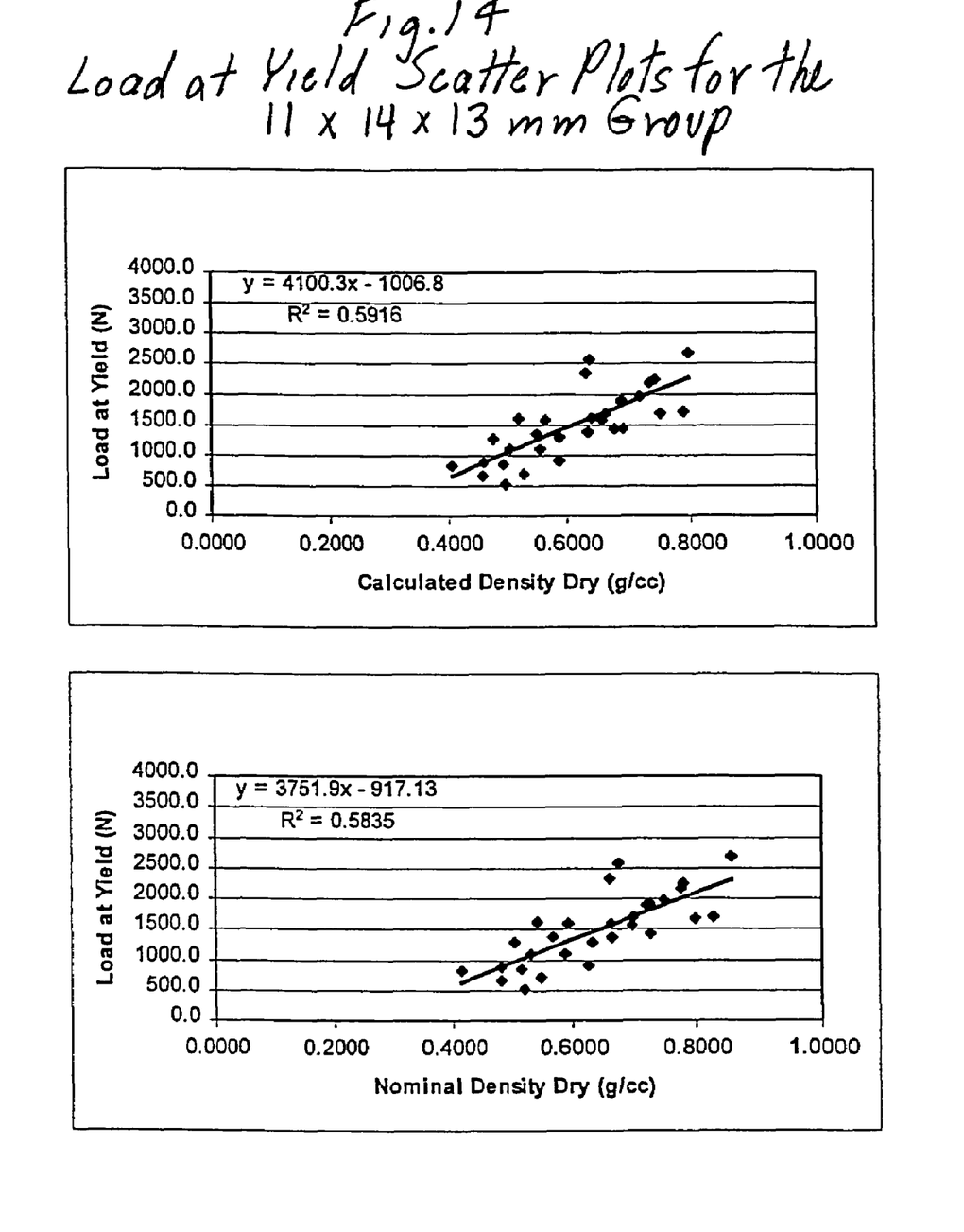
Figure 15:
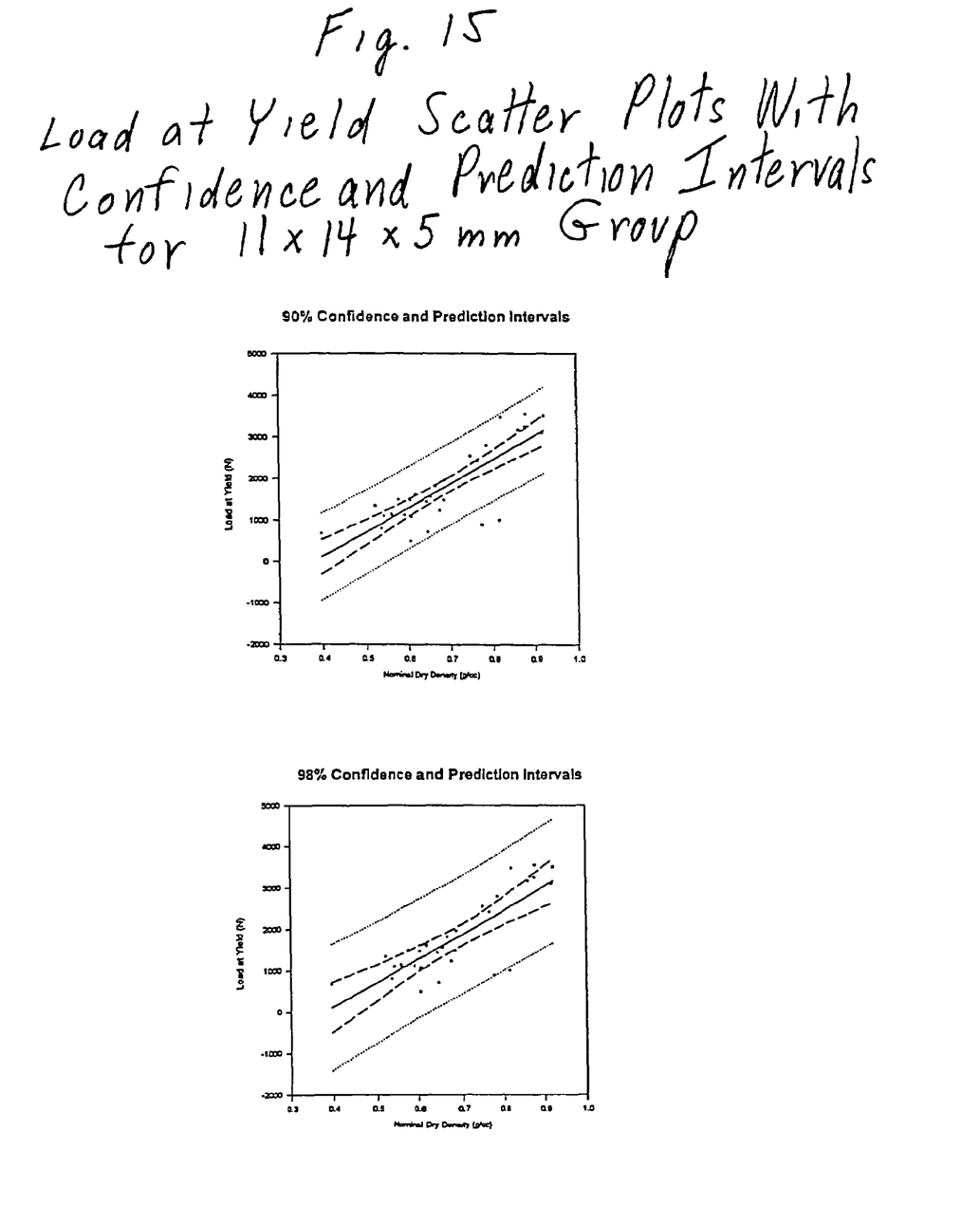
Figure 16:
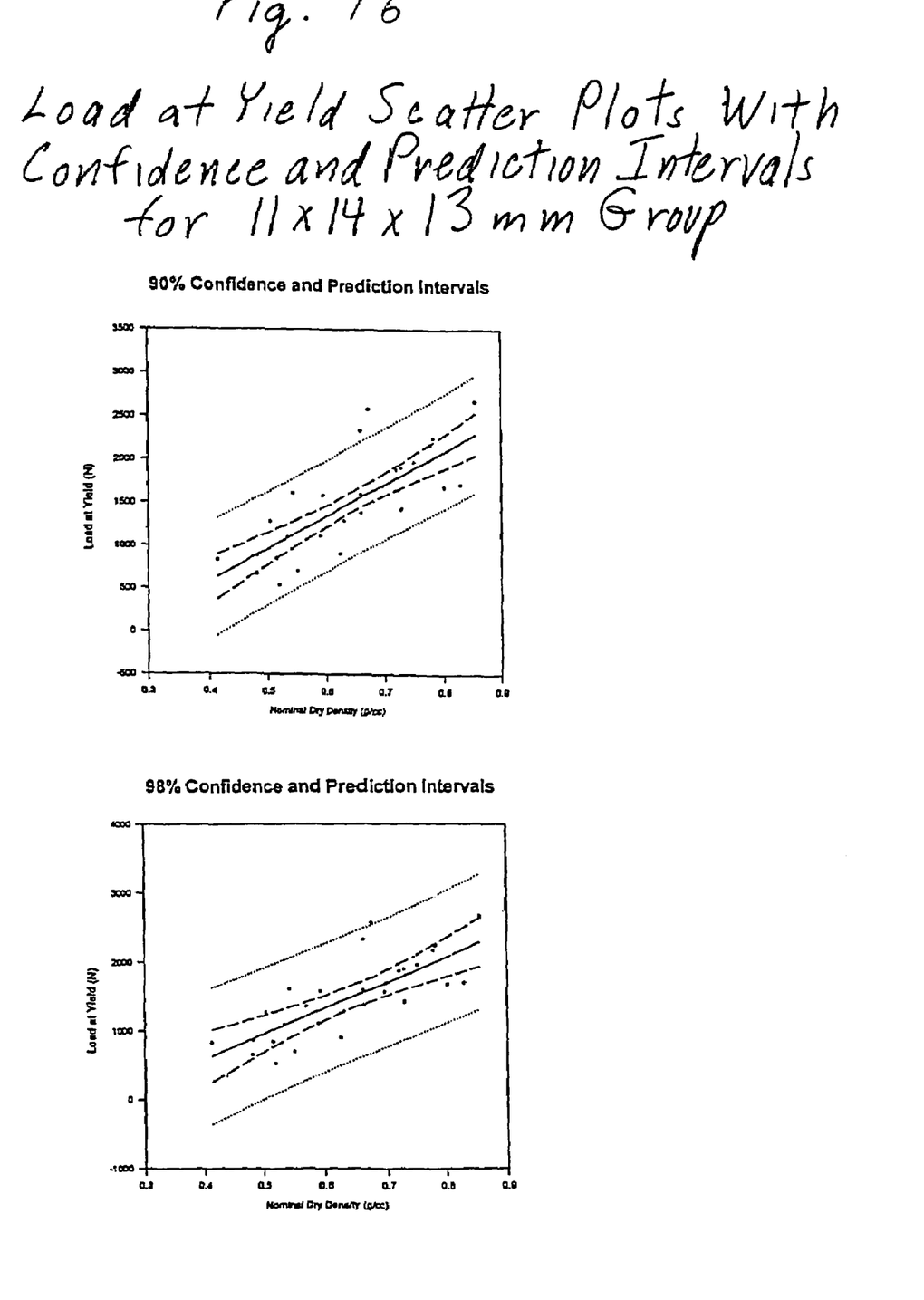

For both specimen groups, dry weight of the specimen is essentially as predictive of strength as calculated dry density. The small change in $r^2$ values between nominal density and calculated density vs. load at yield (FIGS. 13 and 14) is noted.

For both test groups, the difference in average absolute error between a regression equation predicting its own size group, and the cross-prediction on the same group (e.g. 5 mm predicts 5 mm vs. 13 mm predicts 5 mm) was 63N and 81N. This indicates that the cross-prediction ability for different sized machine-cut specimen regression equations is only slightly worse than the predictive ability of the regression equation derived directly from that group.

Absolute error averages in cross-prediction were not significantly different (p>0.05) between the two size groups (Table 8).

It will be understood that various modifications may be made to the embodiments disclosed herein. For example, the order of the tests may be varied. Moreover, the degree to which the bone has been cleaned, freeze dried, or prepared before each or all of the tests are conducted may vary, e.g., the cancellous bone need not be cleaned or it may undergo a complete cleaning cycle before conducting any one or all of the above-identified tests. Further, each of these tests may be used individually or in conjunction with any one or both of the remaining tests to eliminate unsuitable bone from consideration as graft bone. For example, the apparent density test may be used alone or in combination with only the manual compression test to identify a subset of cancellous bone allografts which meet or do not meet necessary strength requirements. Therefore, the above description should not be construed as limiting, but merely as exemplifications of preferred embodiments. Those skilled in the art will envision other modifications within the scope and spirit of the claims appended hereto.

The invention claimed is:

1. A non-destructive method for evaluating the strength of cancellous bone, comprising the steps of: providing a population of cancellous bone; performing at least two of the following tests on each bone in the population: a manual compression test, an apparent density test, and an appearance test; determining a compressive strength for each cancellous bone of said population of cancellous bone based on said at least two tests performed; comparing said determined compressive strength of each cancellous bone against a predetermined compressive strength requirement; and eliminating a subset of cancellous bone from said population of cancellous bone, which subset of cancellous bone fails to meet said predetermined compressive strength requirement.

2. The method for evaluating the strength of cancellous bone according to claim 1, wherein said manual compression test and said apparent density test are performed on each cancellous bone of said population of cancellous bone in order to determine said compressive strength.

3. The method for evaluating the strength of cancellous bone according to claim 1, wherein said manual compression test and said appearance test are performed on each cancellous bone of said population of cancellous bone in order to determine said compressive strength.

4. The method for evaluating the strength of cancellous bone according to claim 1, wherein said apparent density test and said appearance test are performed on each cancellous bone of said population of cancellous bone in order to determine said compressive strength.

5. The method for evaluating the strength of cancellous bone according to claim 1, wherein said manual compression test, said apparent density test and said appearance test are performed on each cancellous bone of said population of cancellous bone in order to determine said compressive strength.

6. The method for evaluating the strength of cancellous bone according to claim 1, wherein said manual compression test includes the steps of: manually compressing each of said cancellous bones to make a subjective determination of said compressive strength of each of said cancellous bones; and removing a cancellous bone from said population of cancellous bones when said manually compressed cancellous bone appreciably deforms.

7. The method for evaluating the strength of cancellous bone according to claim 2, wherein said manual compression test includes the steps of: manually compressing each of said cancellous bones to make a subjective determination of said compressive strength of each of said cancellous bones; and removing a cancellous bone from said population of cancellous bones when said manually compressed cancellous bone appreciably deforms.

8. The method for evaluating the strength of cancellous bone according to claim 3, wherein said manual compression test includes the steps of: manually compressing each of said cancellous bones to make a subjective determination of said compressive strength of each of said cancellous bones; and removing a cancellous bone from said population of cancellous bones when said manually compressed cancellous bone appreciably deforms.

9. The method for evaluating the strength of cancellous bone according to claim 5, wherein said manual compression test includes the steps of: manually compressing each of said cancellous bones to make a subjective determination of said compressive strength of each of said cancellous bones; and removing a cancellous bone from said population of cancellous bones when said manually compressed cancellous bone appreciably deforms.

10. The method for evaluating the strength of cancellous bone according to claim 1, wherein said appearance test includes the steps of: assessing a quality of each of said cancellous bones based on their individual appearance; and assigning each of said cancellous bones with a grade which designates a subjective quality assessment of each of said cancellous bones.

11. The method for evaluating the strength of cancellous bone according to claim 3, wherein said appearance test includes the steps of: assessing a quality of each of said cancellous bones based on their individual appearance; and assigning each of said cancellous bones with a grade which designates a subjective quality assessment of each of said cancellous bones.

12. The method for evaluating the strength of cancellous bone according to claim 4, wherein said appearance test includes the steps of: assessing a quality of each of said cancellous bones based on their individual appearance; and assigning each of said cancellous bones with a grade which designates a subjective quality assessment of each of said cancellous bones.

13. The method for evaluating the strength of cancellous bone according to claim 5, wherein said appearance test includes the steps of: assessing a quality of each of said cancellous bones based on their individual appearance; and assigning each of said cancellous bones with a grade which designates a subjective quality assessment of each of said cancellous bones.

14. A non-destructive method for evaluating the strength of cancellous bone, comprising the steps of: providing a population of cancellous bone; performing at least two of the following tests on each bone in the population, the tests being performed on each bone after the bone has been freeze dried: a manual compression test, an apparent density test, and an appearance test; determining a compressive strength for each cancellous bone of said population of cancellous bone based on said at least two tests performed; comparing said determined compressive strength of each cancellous bone against a predetermined compressive strength requirement; and eliminating a subset of cancellous bone from said population of cancellous bone, which subset of cancellous bone fails to meet said predetermined compressive strength requirement.

15. A non-destructive method for evaluating the strength of cancellous bone, comprising the steps of: providing a population of cancellous bone; performing at least two of the following tests on each bone in the population: a manual compression test, an apparent density test which includes the steps of: cleaning each of said cancellous bones; freeze drying each of said cancellous bones; measuring the dimensions of each of said cancellous bones; determining a volume of each of said cancellous bones from said measured dimensions; weighing each of said cancellous bones; determining an apparent density for each of said cancellous bones; and determining said compressive strength of each of said cancellous bones based on said apparent density; and an appearance test; determining a compressive strength for each cancellous bone of said population of cancellous bone based on said at least two tests performed; comparing said determined compressive strength of each cancellous bone against a predetermined compressive strength requirement; and eliminating a subset of cancellous bone from said population of cancellous bone, which subset of cancellous bone fails to meet said predetermined compressive strength requirement.

16. A non-destructive method for evaluating the strength of cancellous bone, comprising the steps of: providing a population of cancellous bone; performing at least two of the following tests on each bone in the population: a manual compression test, an apparent density test which includes the steps of: cleaning each of said cancellous bones; freeze drying each of said cancellous bones; measuring the dimensions of each of said cancellous bones; determining a volume of each of said cancellous bones from said measured dimensions; weighing each of said cancellous bones; determining an apparent density for each of said cancellous bones; and determining said compressive strength of each of said cancellous bones based on said apparent density; and an appearance test, said manual compression test and said apparent density test being performed on each cancellous bone of said population of cancellous bone in order to determine said compressive strength; determining a compressive strength for each cancellous bone of said population of cancellous bone based on said at least two tests performed; comparing said determined compressive strength of each cancellous bone against a predetermined compressive strength requirement; and eliminating a subset of cancellous bone from said population of cancellous bone, which subset of cancellous bone fails to meet said predetermined compressive strength requirement.

17. A non-destructive method for evaluating the strength of cancellous bone, comprising the steps of: providing a population of cancellous bone; performing at least two of the following tests on each bone in the population: a manual compression test, an apparent density test which includes the steps of: cleaning each of said cancellous bones; freeze drying each of said cancellous bones; measuring the dimensions of each of said cancellous bones; determining a volume of each of said cancellous bones from said measured dimensions; weighing each of said cancellous bones; determining an apparent density for each of said cancellous bones; and determining said compressive strength of each of said cancellous bones based on said apparent density; and an appearance test, said apparent density test and said appearance test being performed on each cancellous bone of said population of cancellous bone in order to determine said compressive strength; determining a compressive strength for each cancellous bone of said population of cancellous bone based on said at least two tests performed; comparing said determined compressive strength of each cancellous bone against a predetermined compressive strength requirement; and eliminating a subset of cancellous bone from said population of cancellous bone, which subset of cancellous bone fails to meet said predetermined compressive strength requirement.

18. A non-destructive method for evaluating the strength of cancellous bone, comprising the steps of: providing a population of cancellous bone; performing at least two of the following tests on each bone in the population: a manual compression test, an apparent density test which includes the steps of: cleaning each of said cancellous bones; freeze drying each of said cancellous bones; measuring the dimensions of each of said cancellous bones; determining a volume of each of said cancellous bones from said measured dimensions; weighing each of said cancellous bones; determining an apparent density for each of said cancellous bones; and determining said compressive strength of each of said cancellous bones based on said apparent density; and an appearance test, said apparent density test and said appearance test being performed on each cancellous bone of said population of cancellous bone in order to determine said compressive strength; determining a compressive strength for each cancellous bone of said population of cancellous bone based on said at least two tests performed; comparing said determined compressive strength of each cancellous bone against a predetermined compressive strength requirement; and eliminating a subset of cancellous bone from said population of cancellous bone, which subset of cancellous bone fails to meet said predetermined compressive strength requirement.

* * * * *